US012626398B2

(12) United States Patent
Kompatscher et al.

(10) Patent No.: US 12,626,398 B2
(45) Date of Patent: May 12, 2026

(54) METHOD FOR MONITORING A SUBJECT POSITION

(71) Applicant: Brainlab AG, Munich (DE)

(72) Inventors: Lukas Kompatscher, Munich (DE); Christina Schill, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 18/281,975

(22) PCT Filed: Dec. 21, 2022

(86) PCT No.: PCT/EP2022/087269
§ 371 (c)(1),
(2) Date: Sep. 14, 2023

(87) PCT Pub. No.: WO2023/131533
PCT Pub. Date: Jul. 13, 2023

(65) Prior Publication Data
US 2024/0153134 A1 May 9, 2024

(30) Foreign Application Priority Data

Jan. 7, 2022 (WO) .................. PCT/EP2022/050291

(51) Int. Cl.
*G06T 7/73* (2017.01)
*A61B 34/20* (2016.01)
*A61N 5/10* (2006.01)
(52) U.S. Cl.
CPC ................. *G06T 7/74* (2017.01); *A61B 34/20* (2016.02); *A61N 5/1049* (2013.01); *A61B 2034/2065* (2016.02); *A61N 2005/1074* (2013.01)

(58) Field of Classification Search
None
See application file for complete search history.

(56) References Cited

U.S. PATENT DOCUMENTS

2005/0234327 A1 10/2005 Saracen et al.
2006/0072699 A1 4/2006 Mackie et al.
(Continued)

FOREIGN PATENT DOCUMENTS

GB 2522914 A1 8/2015

OTHER PUBLICATIONS

International Search Report and Written Opinion for PCT/EP2022/087269, Date of Mailing Apr. 17, 2023, 13 pages.
(Continued)

*Primary Examiner* — Lennin R Rodriguezgonzalez
(74) *Attorney, Agent, or Firm* — Tucker Ellis LLP

(57) ABSTRACT
The disclosed method for monitoring a subject position comprises determining a deviation of a position of a predetermined portion of a subject from a predetermined position of the predetermined portion of the subject, and, based on the deviation, determining correction data, the correction data specifying one or more corrections to be performed on the subject position as part of a position correction procedure and specifying one or more rotational corrections as being excluded from the position correction procedure. The method further comprises setting reference data as a reference for subsequent monitoring of changes of the subject position, wherein the reference data comprises the correction data and initial image data acquired prior to performing the position correction procedure and/or corrected initial image data that has been corrected based on the correction data.

19 Claims, 11 Drawing Sheets

S11
Determine deviation of a position of a predetermined portion of a subject from a predetermined position of the predetermined portion of the subject

S12
Determine correction data based on the deviation

S13
Set reference data as a reference for subsequent monitoring of changes of the subject position

(56) References Cited

U.S. PATENT DOCUMENTS

| 2011/0313228 | A1 | 12/2011 | Handa et al. |
| 2014/0241497 | A1 | 8/2014 | Keall et al. |
| 2021/0339047 | A1 | 11/2021 | Janardhanan et al. |
| 2022/0218298 | A1* | 7/2022 | Gou .................... A61B 6/5264 |

OTHER PUBLICATIONS

Kontaxis, et al. Fast Online Replanning for Interfraction Rotation Correction in Prostate Radiotherapy, Aug. 9, 2017, 9 pages.

* cited by examiner

S11
Determine deviation of a position of a predetermined portion of a subject
from a predetermined position of the predetermined portion of the subject S12
Determine correction data based on the deviation S13
Set reference data as a reference for subsequent monitoring of changes
of the subject position

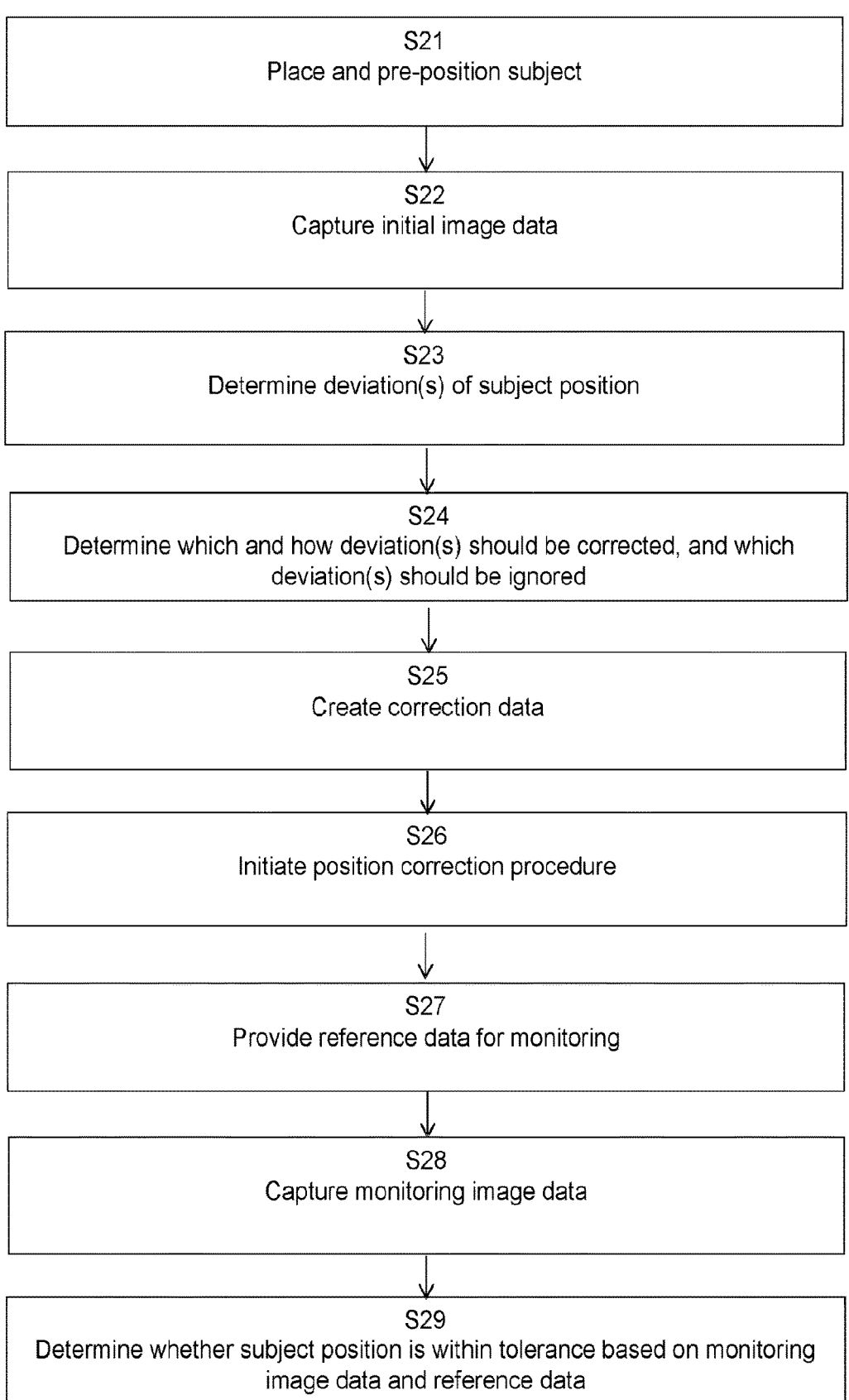

S21
Place and pre-position subject

S22
Capture initial image data

S23
Determine deviation(s) of subject position

S24
Determine which and how deviation(s) should be corrected, and which deviation(s) should be ignored

S25
Create correction data

S26
Initiate position correction procedure

S27
Provide reference data for monitoring

S28
Capture monitoring image data

S29
Determine whether subject position is within tolerance based on monitoring image data and reference data

Fig. 2

METHOD FOR MONITORING A SUBJECT POSITION

FIELD OF THE INVENTION

The present invention relates to a computer-implemented method for monitoring a subject position, an augmented reality system, a medical system, a computer program, a storage medium, a signal wave, a data stream, and a computer.

TECHNICAL BACKGROUND

In medical systems, positioning of subjects, e.g., patient bodies, with respect to pieces of equipment of a medical system, e.g., a radiation beam source or imaging system, is often performed prior to or at the beginning of the operation of some of the pieces of equipment. Subsequently, the position of the subject is often monitored.

At present, it is known to position the subject using previously acquired planning image data, for example comprising CT image data, of at least a portion of the subject. For example, the subject may be arranged such that the portion of the subject has a pre-defined position with respect to pieces of equipment of a medical system. The position may be pre-defined, for example, based on the planning image data. After initial positioning, the subject position may be monitored to detect any changes in position.

Generally, when adjusting a patient position, shifts can be corrected more easily than rotations by adjusting the actual patient position. However, rotations can only be rectified to a very small degree. For example, rotation of the subject support unit, e.g., patient couch, may have an angular limit and/or a shift from side to side or front/back entailed with the angular correction may become too high and/or tilting of the subject support unit will lead movement of the subject due to gravity or an unsafe state for the subject on the subject support.

In some cases, certain rotations or angular deviations, even if they are large, may not be of particular concern. Accordingly, it would be acceptable to not correct the position in terms of these deviations.

However, if the subject is not brought and kept in a position that is within a permissible range around the planned position, many medical systems have implemented features that cause the medical system to not work properly or stop working altogether, for example safety-features.

Accordingly, angular deviations outside of the possible range of correction currently often require adapting the planning image data obtained at the planning stage. This takes a lot of effort and time. Alternatively overriding or circumventing the above-mentioned features is conceivable, but this may not be possible with all systems and may also carry certain risks.

It is an object of the present invention to provide a method that alleviates at least some of the above disadvantages.

The present invention can be used, for example, in connection with a system for image-guided radiotherapy such as VERO®, ExacTrac® and ExacTrac Dynamic®, all products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present disclosure provides a computer-implemented method for monitoring a subject position. The method comprises determining a deviation of a position of a predetermined portion of a subject from a predetermined position of the predetermined portion of the subject. The method further comprises, based on the deviation, determining correction data, the correction data specifying one or more corrections to be performed on the subject position as part of a position correction procedure and specifying one or more rotational corrections as being excluded from the position correction procedure. The method further comprises setting reference data as a reference for subsequent monitoring of changes of the subject position, wherein the reference data comprises the correction data and initial image data acquired prior to performing the position correction procedure and/or corrected initial image data that has been corrected based on the correction data.

GENERAL DESCRIPTION OF THE INVENTION

In this section, a description of the general features of the present invention is given for example by referring to possible embodiments of the invention.

The present disclosure provides a computer-implemented method for monitoring a subject position. The method comprises determining a deviation of a position of a predetermined portion of a subject from a predetermined position of the predetermined portion of the subject. The method further comprises, based on the deviation, determining correction data, the correction data specifying one or more corrections to be performed on the subject position as part of a position correction procedure and specifying one or more rotational corrections as being excluded from the position correction procedure. The method further comprises setting reference data as a reference for subsequent monitoring of changes of the subject position. The reference data may comprise the correction data and initial image data acquired prior to performing the position correction procedure. Alternatively or in addition, the reference image data may comprise corrected initial image data that has been corrected based on the correction data.

An advantage of the claimed method is that in case performing a correction of the rotation is technically difficult or not possible, would yield an unsafe state for the subject, or would impede the application, e.g., reduce accuracy or reliability, the rotation can be excluded from the correction, thereby alleviating the problem brought about by the correction. At the same time, it can be avoided that, during the subsequent monitoring, operation is impeded by the detected persisting rotational deviation.

In particular, misalignment or deviation from the target orientation pertaining to inner organs of the subject (rather than for example an extremity that can be moved relatively easily, often without repositioning the entire patient), particularly, rotations of the inner organ with respect to the planning image data, may be hard to correct. As the entire patient may have to be moved, for inner organs correction is more difficult than that of, for example, a head or extremities of a subject. Therefore, in these cases the method of the present disclosure is particularly useful.

In general, a position and/or a deviation of a position and/or a correction of a position may be characterized by a set of rotations and translations, also referred to as shifts, i.e., there may be up to six degrees of freedom for deviations and/or corrections. In other words, the position is a 6 DOF position, and accordingly includes orientation.

The predetermined portion of the subject may be or comprise an inner organ, particularly an extracranial organ like the prostate, pancreas, gallblader, lung and/or liver. The predetermined portion may be a region of interest or may be comprised in a region of interest in the image data.

The predetermined position may be a target position, e.g., determined during a planning phase, that is deemed most suitable for the subsequent procedure or application during which the subject will be monitored. It may be determined, for example, by a person, and/or it may be stored as part of planning data.

Determining correction data based on the deviation may comprise determining which rotations and/or translations of the subject would cause the rotational and/or translational component of the position of the predetermined portion to correspond to the rotational and/or translational component of the predetermined position. In other words, it may comprise determining which rotations and/or rotations would lead to the predetermined portion of the subject being in the predetermined position after performing all determined rotations and/or translations. The determining may then further comprise determining one or more of the rotations and/or translations to be excluded from the correction procedure.

A position correction procedure may, particularly, comprise changing the position of the entire subject. This generally also entails change of the position of the predetermined portion.

The correction data specifying one or more rotational corrections as being excluded from the position correction procedure may, for example, include storing data, e.g., an identifier or tag or metadata, indicating that the rotational correction is to be excluded.

Setting reference data as a reference for subsequent monitoring of changes of the subject position may mean that the reference data may be used for determining whether or not a subject position is still within tolerance or has moved out of tolerance. For the sake of doing so, the correction may be applied to the initial image data and then the corrected initial image data may be compared to monitoring image data and deviations from the corrected initial image data will be used for determining whether the position is out of tolerance. Alternatively, the initial image data may not be corrected, but included, as is, in the reference data. The reference data may then also comprise the correction data. The correction data can be used to determine whether or not a deviation between the monitoring image data and initial image data is acceptable. For example, the angle of the excluded rotational deviation may always be taken into account when determining whether changes of position during monitoring are out of tolerance. In terms of rendering the image data, e.g., when overlaying monitoring image data with other image data, the correction data may either be applied to the initial image data to obtain corrected initial image data and the corrected image data and monitoring image data may be overlayed. Alternatively or in addition, the correction data may be used for correcting the monitoring image data and overlaying the corrected monitoring image data, e.g., on the initial image data or the planning image data. This will be outlined below in more detail.

In other words, the method of the present disclosure may entail applying the correction to the initial image and then proceeding only on the basis of the corrected initial image as a reference and it may entail storing the initial image data and the associated correction data together and using both as reference for the monitoring. Even when proceeding with the corrected initial image data as a reference, the correction data may be stored with the corrected initial image data, for example for use in rendering different overlayed views.

It is noted that optionally another image may be captured after performing the position correction procedure and prior to monitoring for supplementary use in monitoring.

According to the present disclosure, determining correction data may comprise determining, for each rotational deviation of the predetermined portion of the subject, whether the rotational deviation should be corrected by means of the position correction procedure. Determining the correction data may further comprise, in response to determining that the rotational deviation should not be corrected, specifying a corresponding rotational correction as being excluded from the position correction procedure.

In the present disclosure, determining whether the rotational deviation should be corrected may comprise receiving a user selection via a user interface and/or may be performed automatically on the basis of pre-determined criteria, in particular, by determining whether the rotational deviation exceeds a predetermined threshold. This may also entail a semi-automatic determination wherein, when predetermined criteria are met, an exclusion of a rotational deviation may be automatically suggested to the user via a user interface and, the correction may be excluded only in case a user input confirming the exclusion is received.

As an example, determining whether a rotational deviation should be corrected may comprise determining, for each of the rotational deviations, whether the rotation angle of the deviation exceeds a pre-determined threshold, and, if so, determining that the deviation should not be corrected or outputting a suggestion to a user interface to exclude the deviation from the position correction procedure.

The above-mentioned threshold may be different for each rotation axis and/or direction and may also be different depending on the medical system setup at hand. For example, tilts out of a horizontal plane may have a lower threshold than a rotation around a vertical axis.

The corresponding rotational correction, i.e., the rotational correction corresponding to a rotational deviation, may be the rotational correction that would correct the rotational deviation.

An advantage of the above is that the method can be applied flexibly, with different systems and in different situations and allowing for case-specific exclusions from the position correction procedure and taking them into account for monitoring.

According to the present disclosure, the determining of the deviation may comprise determining the position of the predetermined portion of the subject based on the initial image data of the predetermined portion of the subject acquired prior to monitoring image data and determining the position of the predetermined portion of the subject based on planning image data of the predetermined portion of the subject acquired prior to acquiring the initial image data. The determining of the deviation may further comprise determining a 6 DOF difference between the determined positions.

For example, if the predetermined portion is an inner organ, determining the deviation may be based on the position of the inner organ in the planning image data and in the initial image data. Although positional deviations of the subject, as a whole, may also be detectable by determining deviations of positions of other parts of the subject, using the predetermined portion may, in some cases, yield better results. The relative position of the predetermined portion and other portions may have changed. In case the predetermined portion is the region of interest for the application at hand, results may thus in some cases be more precise when using said predetermined portion for determining the deviation. The deviation of positions of other portions of the subject may optionally be used as supplementary data.

The method of the present disclosure may comprise, after determining the deviation, triggering an automatic position correction procedure of the subject position, based on the correction data. The position correction procedure may exclude the one or more rotational corrections specified as being excluded from the correction procedure in the correction data.

Excluding the correction from the correction procedure means that the correction procedure only includes translational corrections and/or rotational corrections that are not specified as being excluded. Thus, for example, the subject may only be shifted in one or more directions and/or only rotated around one or more rotation axis that do not correspond to the excluded rotational corrections. The exclusion refers to intentional changes in patient position, e.g., a patient inadvertently tilting during a translational movement is not to be interpreted as the correction procedure including the (inadvertent) tilting.

As an example, the subject may be mounted on a subject support unit, e.g., a patient couch, during the correction procedure. In particular, the subject may be mounted such that the subject will be moved together with subject support unit. The correction procedure may then comprise changing the position of the subject support unit, thereby indirectly changing the position of the subject. Triggering an automatic position correction procedure may comprise generating and providing control signals that cause one or more drives, e.g., motors, to change the position of the subject support unit.

By excluding the excluded rotational corrections, technical limitations can be accounted for and/or it can be avoided that the subject is brought into a position that is detrimental for the application at hand and/or for the safety of the subject, for example, as explained above.

In the present disclosure, each of the planning image data and the initial image data may comprise image data of an inner, particularly extracranial, organ of the subject and the predetermined portion may include the inner organ of the subject. The deviation may be determined at least on the basis of a position of the inner organ. The planning image data may optionally further comprise surface image data of the subject.

Examples for inner, extracranial organs are a prostate, pancreas, gallblader, lung and/or liver. At least for some of these organs, depending on the application, rotational deviations may be uncritical enough to be ignored and, accordingly, may be excluded from a position correction.

As an example, the image data of the inner organ may be volume image data obtained by means of volume imaging methods.

Volume image data, in the present disclosure, refers to image data that allows for imaging the entire volume of the subject, in particular including internal structures of the subject, e.g., internal patient anatomy, which may include inner organs and/or bones, for example. As such, volume image data particularly may comprise images of the predetermined portion of the subject, e.g., inner organs. Examples for imaging methods to obtain volume image data, i.e., volume imaging methods, comprise CT imaging, cone beam CT imaging, X-ray imaging, ultrasound imaging, and/or MRT imaging. More specifically, exemplary volume imaging methods comprise monoscopic or stereoscopic X-ray images, portal imaging, ultrasound, MRI, CBCT, or the like. It is noted that in the present disclosure volume imaging may, but need not necessarily, yield 3D images. In other words, volume image data may comprise 3D and/or 2D image data.

It is noted that, when obtaining the volume image data for the planning image data and/or the initial image data, markers may be present in the predetermined portion of the subject, e.g., in the inner organ. For example, these may be implanted markers, particularly fiducial markers, e.g., radiopaque markers, MR markers, or other markers visible in the respective volume imaging data.

Surface image data, in the present disclosure, may comprise image data that allows for deriving a, in particular 3D, shape of the surface of the subject. For example, known 3D imaging devices, e.g., a camera including a surface camera and optionally including a thermographic camera, e.g., an infrared camera, and/or a surface scanner, such as a structured light camera, time of flight sensor, LIDAR, laser scanner, or stereoscopic optical camera, may be used for acquiring surface image data. Alternatively or in addition, surface image data may also be obtained from volume image data, e.g. CT image data, by calculating a contour of the surface from the volume image data.

As mentioned above, in the present disclosure the monitoring of changes of the subject position may be based on monitoring image data. The reference data and the monitoring image data may each comprise surface image data of the subject and monitoring the subject position may comprise surface imaging. In particular, monitoring may comprise detecting deviations of the surface image data of the monitoring image data from the surface image data of the reference data.

Surface imaging may, for example, be performed by means of a surface camera and/or a surface scanner. In case of the monitoring image data, the surface imaging may be performed continuously and/or at predetermined times and/or time intervals.

Determining deviations of the surface image data may be performed using known techniques, for example based on features of the surface and/or markers on the surface and/or point clouds of surface image data. For example, an ICP algorithm may be used to find the difference between two point clouds.

An advantage is that surface imaging, particularly where surface imaging is performed by means of a camera or surface scanner, allows for easy and fast image acquisition that is not harmful to the subject.

As mentioned above, in the present disclosure the monitoring of changes of the subject position may be based on monitoring image data. The reference data and the monitoring image data may each comprise volume image data of the subject and monitoring the subject position may comprise volume imaging. In particular, the monitoring may comprise detecting deviations of the volume image data of the monitoring image data from the volume image data of the reference data.

An advantage is that the volume imaging provides high accuracy data and also allows for observing the position of portions of the subject below the surface, e.g., inner organs. This may then include the above-mentioned predetermined portion of the subject.

In particular, the monitoring may comprise the above-described surface imaging and the above-described volume imaging, and the surface imaging may be configured to obtain image data more frequently than the volume imaging. In particular, the surface imaging may be configured to obtain image data continuously.

In particular, the volume imaging may be X-ray imaging and the surface imaging may be performed by means of a surface camera or a surface scanner. X-ray imaging may be performed only when triggered manually or only at times or time intervals determined so as to keep the overall dose below a predetermined threshold. The overall dose may be determined based on an expected monitoring time and expected dose per X-ray image. It is noted that imaging is considered to be continuous if performed, without intentional interruptions, at a high frequency, for example, at a frequency of equal to or more than 1 Hz. In particular, continuous imaging may be performed at a frequency of equal to or more than 5 Hz, in particular equal to or more than 10 Hz, in particular equal to or more than 20 Hz, or more. The frequency of the surface imaging and/or whether it is to be performed continuously, may be predetermined, for example, based on required time resolution for the application at hand and/or expected speed and/or range of subject movement and/or available computing resources for processing the image data.

Thus, data from the surface imaging can be supplemented with data from the volume imaging. This allows for improving overall accuracy, and particularly allows for continuous monitoring, without significantly increasing harmful effects of the volume imaging on the subject.

The monitoring of subject position may comprise, in response to the subject position moving out of a predetermined tolerance, triggering an output of a warning and/or output of a correction suggestion to an operator and/or triggering an automatic position correction procedure. For example, one or more control signals may be issued to a subject support unit to move in such a manner as to correct the subject position of the subject placed on the subject support unit. Thus, it can be ensured that the subject does not move too much away from a target position, e.g., the position at which the monitoring started, i.e., the position obtained by the (initial) position correction procedure.

The automatic position correction procedure may optionally comprise one or more rotations, in particular, even a rotation around the same axis as a rotation that had been excluded from the correction procedure. Contrary to larger rotational deviations and corresponding corrections prior to the monitoring, usually the rotational deviations during monitoring may be relatively small, which may allow for correction without bringing about the disadvantages of larger rotational corrections. The automatic position correction may, alternatively or in addition to one or more rotations, comprise one or more translations.

Optionally, one or more rotational and/or translational changes of the subject position, in particular one or more rotational and/or translational changes that cause the subject position to move out of the predetermined tolerance, may be ignored. The one or more rotational and/or translational changes to be ignored may be determined by a user selection and/or automatically based on predetermined criteria. In particular, the one or more rotational and/or translational changes may be excluded from triggering an output of a warning and/or output of a correction suggestion to an operator and/or triggering an automatic position correction procedure.

The automatic and/or user selected exclusion may be performed similarly to the excluding of a rotation prior to the position correction procedure. For example, as mentioned above, there are rotational deviations that may safely be ignored for performing the initial correction procedure. This may also be true when these rotational deviations occur at a later time during monitoring. The possibility to exclude such rotations may improve efficiency, as it decreases the number of correction procedures initiated and/or alarms to be handled.

The reference data of the present disclosure may comprise volume image data that is used as a reference for volume imaging-based monitoring. Surface image data corresponding to the volume image data of the reference data may be set as a reference for monitoring by means of surface imaging. Alternatively, a deviation in the surface image data corresponding to the volume image data may be set as acceptable or a deviation in the surface image data corresponding to the volume image data may be set to zero or a deviation in the surface image data corresponding to the volume image data may be set to the deviation of the volume image data.

Alternatively, the reference data may comprise surface image data that is used as a reference for surface-based monitoring. Volume image data corresponding to the surface image data of the reference data may be set as a reference for monitoring by means of volume imaging. Alternatively, a deviation in the volume image data corresponding to the surface image data may be set as acceptable or a deviation in the volume image data corresponding to the surface image data may be set to zero or a deviation in the volume image data corresponding to the surface image data may be set to the deviation of the surface image data.

In other words, it may be possible, when monitoring is performed using both surface image data and volume image data for the monitoring, to use one of the surface image data and the volume image data as main reference data. Thus, for example, when a determination has been made with respect to the main image data, the respective determination does not have to be made for the other image data or may be overridden by the determination result for the main image data. This allows for resolving potential discrepancies between determinations made with different imaging methods.

It is noted that, in general, volume image data and surface image data are deemed to be corresponding image data in case they are obtained at matching times. This may entail the use case of concurrently taken images, with deviations, for example, of up to 0.5 s. It may also entail, e.g., in case that during the monitoring volume image data is obtained less frequently than the surface image data, that, at any given time, the current surface image data is considered as corresponding to the most recent volume image data.

The method of the present disclosure may comprise rendering, on a user interface, a first view, wherein planning image data are overlayed with monitoring image data. Alternatively or in addition, the method of the present disclosure may comprise rendering, on the user interface, a second view, wherein initial image data are overlayed with monitoring image data. Alternatively or in addition, the method of the present disclosure may comprise rendering, on the user interface, a third view, wherein corrected initial image data are overlayed with planning image data. Alternatively or in addition, the method of the present disclosure may comprise rendering, on the user interface, a fourth view, wherein corrected initial image data are overlayed with monitoring image data. Alternatively or in addition, the method of the present disclosure may comprise rendering, on the user interface, a fifth view, wherein initial image data are overlayed with monitoring image data corrected using the correction data.

In case of the first view, there will be a discrepancy between the overlayed image data in terms of the rotation excluded from the position correction procedure. Optionally, based on the correction image data, the monitoring image data to be overlayed with the planning image data may also be corrected by the excluded rotation. This removes the discrepancy in terms of the excluded rotation.

In case of the second view, the user is presented with the current position as compared to the position prior to the correction procedure.

Similarly to the first view, in case of the third view, there will be a discrepancy between the overlayed image data in terms of the rotation excluded from the position correction procedure. Optionally, based on the correction image data, the corrected initial image data to be overlayed with the planning image data may also be corrected by the excluded rotation. This removes the discrepancy in terms of the excluded rotation.

In case of the fourth view and the fifth view, any discrepancy between the overlayed image data directly reflects changes of the subject position during the monitoring. The views can be obtained by applying the correction to the initial image data or applying an inverse correction on the monitoring image data based on the correction data, respectively.

Different views allow for meeting different demands depending on the application and technical context at hand, thereby improving reliability.

The present disclosure also provides a method comprising the computer-implemented method of the present disclosure.

The method of the present disclosure may comprise rendering, on a/the user interface, a user interface element indicating that one or more rotational corrections are currently excluded from the position correction procedure and/or indicating information on the one or more rotational corrections that are currently excluded, in particular the corresponding rotation axis and/or the direction and/or the amount of the deviation. As an example, the user interface element may comprise information in the form of text, e.g., stating "0°" instead of "5°" for a given excluded rotation of 5°, and/or may optionally add a symbol, e.g., "Δ" or any other predetermined symbol, next to monitored values that had previously been set to 0°, which means they have been excluded from the correction. Thus, it is indicated that deviations from the planning data are actually different from the monitored values rendered on the user interface. Thus, the method allows for preventing errors due to the user not being made aware of the excluded correction.

Optionally, the method of the present disclosure may comprise rendering, on the user interface, a selection option for switching between at least two of the first view, the second view, the third view, the fourth view, and the fifth view. For example, a user interface element, e.g., a drop down menu, a button, and/or toggle switch, may be rendered on the user interface to receive user input for switching between the views. Accordingly, the user can quickly change to a view that is currently required or advantageous, e.g., depending on the current technical requirements.

Alternatively or in addition, the method may comprise rendering, on the user interface, a user interface element indicating which of the views is currently rendered. The user interface element indicating which of the views is currently rendered may include additional information on the current view, e.g., in addition to identifying which of the views is currently rendered, it may also provide information on the respective view, e.g., information on an excluded rotation. Thus, the method allows for preventing errors due to mix-up of the views.

The method of the present disclosure may comprise acquiring the planning image data, in particular the volume image data and, optionally, the surface image data. For example, acquiring the planning image data may comprise capturing volume image data, e.g., CT image data, and/or surface image data. In addition, acquiring the planning image data may comprise post-processing, e.g., at a planning workstation at a later time than the capturing session, e.g., image processing and/or annotation. For example, image processing may comprise registering images comprised in the volume and/or surface image data and/or calculating surface image data, e.g., a contour of the subject, from volume image data. Annotating may comprise adding digital markers and/or tagging portions of the image and/or selecting portions of the image, in particular, a region of interest in the volume image data and/or an area of interest in the surface image data.

Alternatively or in addition, the method of the present disclosure may comprise acquiring the initial image data, in particular the volume image data and, optionally, the surface image data, particularly after acquiring the planning image data. Acquiring the initial image data may, for example, comprise acquiring volume image data by means of an X-ray imaging device and/or surface image data by means of a surface camera and/or a surface scanner. For example, the initial image data may be acquired at the beginning of a monitoring session after placing and optionally pre-positioning a subject. To obtain corresponding volume image data and surface image data, the volume imaging and surface imaging for the initial image data may be performed within a period of time of less than 10 s, in particular less than 1 s, preferably less than 0.5 s, preferably concurrently. The initial image data may be captured at a different time, particularly a different day, and/or at a different location than the planning image data.

Alternatively or in addition, the method of the present disclosure may comprise, in response to a/the triggering of an automatic position correction procedure, performing the position correction procedure by automatically moving a/the subject support unit so as to correct the subject position, the position correction procedure excluding the one or more rotational corrections specified as being excluded from the correction procedure in the correction data. As an example, triggering the automatic position correction procedure may comprise sending one or more control signals to a controller of the subject support unit, which controls one or more drives, e.g., in the form of a motor, so as to move the subject support unit in accordance with the control signals. Alternatively, the control signals may be used to directly control the drive(s). Alternatively, a visual representation of the control signals, specifically the correction they represent, may be displayed on a display device, e.g., for review and/or adjustment and/or confirmation by a user.

Alternatively or in addition, the method of the present disclosure may comprise acquiring monitoring image data, in particular the volume image data and, optionally, the surface image data, particularly after acquiring the planning image data. In particular, the method may comprise acquiring the monitoring image data continuously and/or at least at predetermined times and/or intervals. Acquiring the monitoring image data may, for example, comprise acquiring volume image data by means of an X-ray imaging device and/or surface image data by means of a surface camera and/or a surface scanner. In particular, the volume image data and/or the surface image data may be acquired by means of the same imaging devices as the initial image data.

Alternatively or in addition, the method of the present disclosure may comprise creating control data for controlling medical equipment, in particular, for controlling a radiation beam source to emit a treatment beam and/or to perform a beam stop. As an example, the control data may be created in response to determining, as part of the monitoring, that the subject position is not within a predetermined tolerance, and the created control data may be configured to instruct the radiation beam source to perform a beam stop.

It is noted that any of the method steps of the present disclosure that are performed by devices other than a computing system, may be controlled by a computing system, e.g., the computing system of the present disclosure. In the present disclosure, the computing system of the claims is also sometimes referred to as a computer.

The present disclosure also provides a medical system configured to carry out the method of the present disclosure, particularly the method outlined above. In particular, the medical system may comprise a computing system that may, for example, be configured to carry out and/or trigger and/or control any of the steps of the present disclosure. Alternatively or in addition, the medical system may comprise one or more imaging devices configured to, in particular triggered and/or controlled by means of the computing system, obtain the initial image data and/or the monitoring image data, in particular, an X-ray imaging device configured to obtain the volume image data and/or a surface scanner and/or a surface camera configured to obtain the surface image data.

The medical system may further comprise a medical device, for example a radiation treatment apparatus or a radiation beam source for radiation treatment of a subject or another piece of medical equipment. In particular, the medical device may be configured to be controlled by means of the computing system. Alternatively or in addition, the medical system may comprise a subject support unit, e.g., a couch, configured to automatically correct a subject position, in particular triggered and/or controlled by means of the computing system.

The present disclosure also provides a computer program which, when the program is executed by a computer or when loaded onto a computer, causes the computer to carry out the method steps of the method of the present disclosure. The present disclosure also provides a program storage medium on which the computer program is stored. The present disclosure also provides a computer comprising at least one processor and a memory and/or the program storage medium, wherein the program is running on the computer or loaded into the memory of the computer. The present disclosure also provides a signal wave or a digital signal wave, carrying information which represents the program. The present disclosure also provides a data stream which is representative of the program.

The features and advantages outlined above in the context of the method similarly apply to the augmented reality system, the medical system, the computer program, the program storage medium storing the program, the signal wave, the data stream, and the computer described herein.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning, position monitoring, and imaging. For this reason alone, no surgical or therapeutic activity and in particular no surgical or therapeutic step is necessitated or implied by carrying out the invention.

Further features, examples, and advantages will become apparent from the detailed description making reference to the accompanying drawings.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data"

can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the data-base to the computer. The computer acquires the data for use as an input for steps of determining data. The determined data can be output again to the same or another database to be stored for later use. The database or database used for implementing the disclosed method can be located on net-work data storage device or a network server (for example, a cloud data storage device or a cloud server) or a local data storage device (such as a mass storage device operably connected to at least one computer executing the disclosed method). The data can be made "ready for use" by perform-ing an additional step before the acquiring step. In accor-dance with this additional step, the data are generated in order to be acquired. The data are for example detected or captured (for example by an analytical device). Alternatively or additionally, the data are inputted in accordance with the additional step, for instance via interfaces. The data gener-ated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substan-tial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Analytical Devices

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electro-magnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treat-ment body part within the analytical image. It can for example be easier to identify an indicator body part which correlates with changes in the position of the treatment body part and for example the movement of the treatment body part. Tracking an indicator body part thus allows a move-ment of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indica-tors") can be tracked using marker detection devices. The position of the marker indicators has a known (predeter-mined) correlation with (for example, a fixed relative posi-tion relative to) the position of indicator structures (such as the thoracic wall, for example true ribs or false ribs, or the diaphragm or intestinal walls, etc.) which for example change their position due to vital movements.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation com-prises or consists of particles (for example, sub-atomic particles or ions) or electromagnetic waves which are ener-getic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radio-therapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treat-ment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/health-care_us_elekta_vmat.php and http://www.varian.com/us/oncology/treatments/treatment_techniques/rapidarc.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radio-logical imaging methods) such as for instance computed tomography (CT) and cone beam computed tomography (CBCT, such as volumetric CBCT), x-ray tomography, magnetic resonance tomography (MRT or MRI), conven-tional x-ray, sonography and/or ultrasound examinations, and positron emission tomography. For example, the medi-cal imaging methods are performed by the analytical devices. Examples for medical imaging modalities applied by medical imaging methods are: X-ray radiography, mag-netic resonance imaging, medical ultrasonography or ultra-sound, endoscopy, elastography, tactile imaging, thermog-raphy, medical photogr aphy and nuclear medicine functional imaging techniques as positron emission tomog-raphy (PET) and Single-photon emission computed tomog-raphy (SPECT), as mentioned by Wikipedia.

The image data thus generated is also termed "medical imaging data". Analytical devices for example are used to generate the image data in apparatus-based imaging meth-ods. The imaging methods are for example used for medical diagnostics, to analyse the anatomical body in order to generate images which are described by the image data. The imaging methods are also for example used to detect patho-logical changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded ana-tomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Fixed (Relative) Position

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein

FIG. 2 illustrates a flow diagram of another method according to the present disclosure;

DESCRIPTION OF EMBODIMENTS

Figure 1:
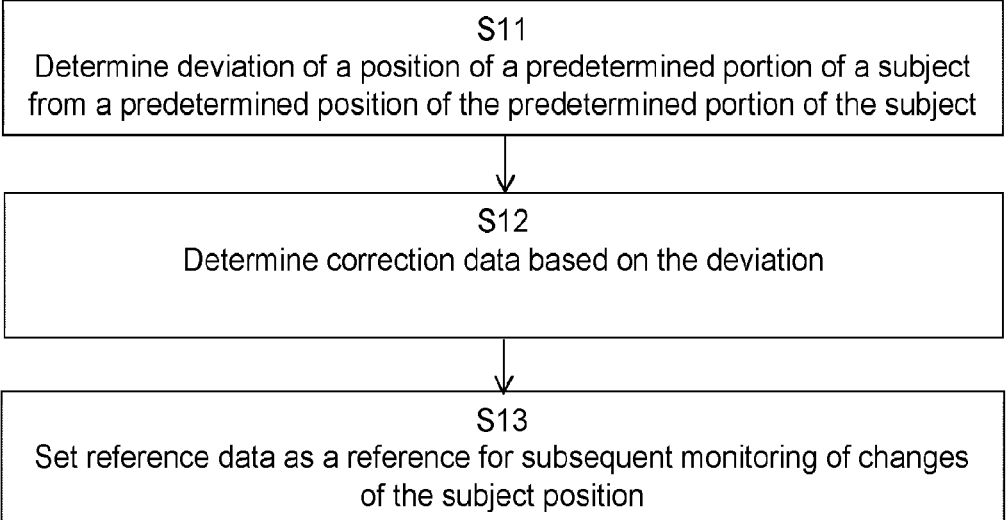
FIG. 1 illustrates a flow diagram of a method according to the present disclosure.

FIG. 1 illustrates an exemplary method according to the present disclosure.

In step S11, a deviation of a position of a predetermined portion of a subject from a predetermined position of the predetermined portion of the subject is determined.

In step S12, based on the deviation, correction data are determined. The correction data specify one or more cor-rections to be performed on the subject position as part of a position correction procedure and one or more rotational corrections as being excluded from the position correction procedure.

In step S13, reference data is set as a reference for subsequent monitoring of changes of the subject position.

The reference data may comprise the correction data and initial image data acquired prior to performing the position correction procedure. Alternatively or in addition it may comprise corrected initial image data that has been corrected based on the correction data.

FIG. 2 illustrates an exemplary method according to the present disclosure.

In step S21, prior to the monitoring, e.g. at the beginning of a monitoring session, a subject may be placed in the range of the imaging device(s) used for monitoring, for example on a subject support unit. Pre-positioning of the subject may be performed, e.g., a rough alignment of the subject. Pre-positioning may be performed, for example, by detecting markers on the surface of the subject, e.g., tattoos. The detection of markers may, for example, be performed using a/the surface camera.

In step S22, initial image data is captured, for example volume image data by means of an X-ray imaging device and surface image data by means of a surface camera.

In step S23, deviations of the position of the subject, in particular of the predetermined portion of the subject, are determined based on the initial image data, which represent the actual position, and planning image data, which represent the target position.

The planning image data may be based on previously acquired CT image data of the subject, particularly the predetermined portion of the subject. The planning image data may comprise, in addition to volume image data, a representation of the shape of the surface of the subject derived from the volume image data and/or acquired by a surface camera or scanner. In the planning image data, the predetermined portion and/or a region of interest (ROI) and or area of interest may be identified.

Next, in step S24, it is determined which deviations should be corrected, how they should be corrected, and which deviations should be ignored. For example, it may be determined for each of six degrees of freedom (three rotations and three translations) whether a correction should be performed and what corrective movement is required, e.g., which direction and by what amount.

In step S25, correction data is then created, the correction data specifying which deviations to correct in a correction procedure and how and which deviations to ignore or exclude from a correction procedure. Then, in step S26, a position correction procedure may be initiated, e.g., by generating a control signal for a controller of the subject support unit, based on the correction data.

In step S27, reference data may be obtained and provided for the monitoring. For example, the correction data may be applied to the initial image data to obtain corrected image data. The corrected image data is corrected based on the correction data, i.e., corrected to include all but the excepted corrections. The corrected initial image data may be provided as reference data for the monitoring. Alternatively or in addition, the initial image data, specifically, the not-corrected initial image data, and the correction data may be provided as reference data for the monitoring. Step S27 need not be performed after step S26. The order may be reversed or they may be performed concurrently, for example.

Monitoring may be performed by capturing monitoring image data in step S28. Specifically, monitoring may comprise repeatedly capturing surface image data of the subject, e.g., from the surface camera, and/or volume image data of the subject, e.g., from the X-ray imaging device. The image data is referred to as monitoring image data.

The monitoring may entail, in step S29, determining whether a subject position or a subject movement is within tolerance. The reference data may be used for the determination. For example, a deviation of the position in the monitoring image data from the position in the corrected initial image data may be determined. Alternatively, the correction image data may be used to determine whether deviations between the initial image data and the monitoring image data are within tolerance.

Figure 3:
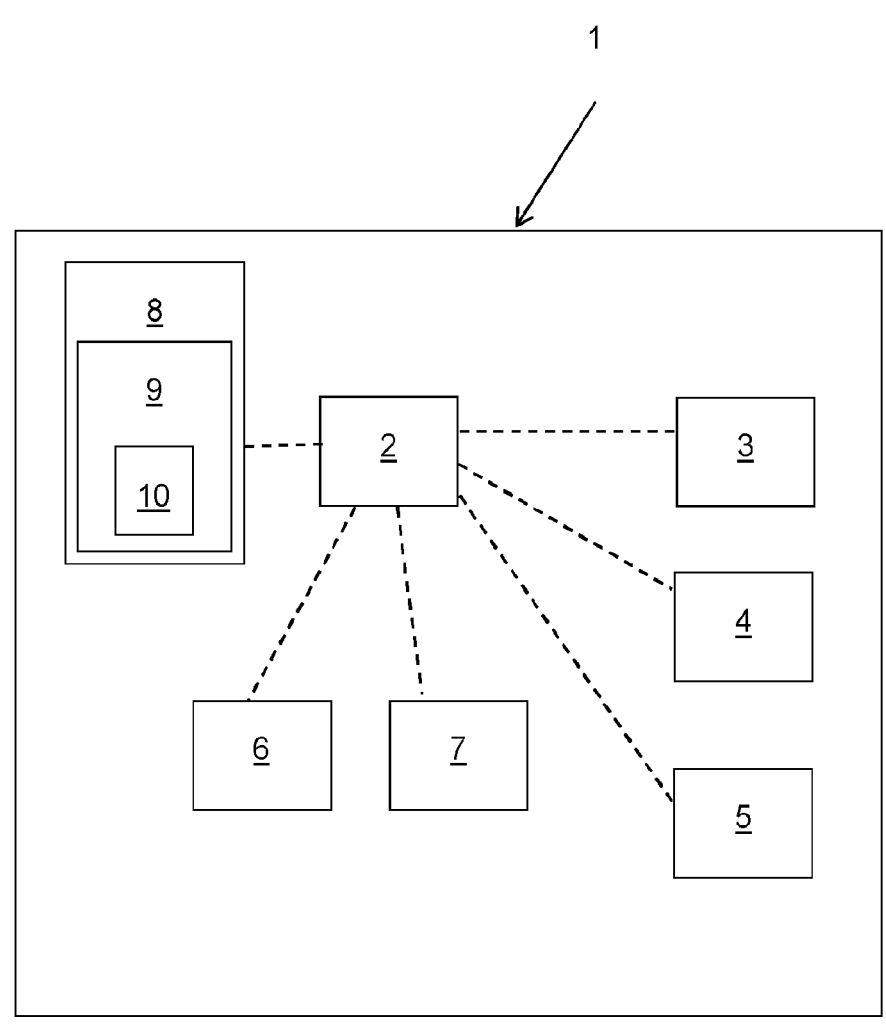
FIG. 3 is a schematic illustration of the system according to the present disclosure.

FIG. 3 is a schematic illustration of an exemplary medical system 1 according to the present disclosure.

The system comprises a computer or computing system 2, imaging devices 3, 4, and 5, each optionally connected to the computing system via a data connection. For example, imaging device 3 may be an X-ray imaging device, imaging device 4 may be a surface camera, and imaging device 5 may be a CT imaging device. Other numbers and types of imaging devices are conceivable, however. The system further comprises a medical device 6, for example a radiation beam source, also referred to as treatment beam source, or a radiation treatment apparatus including the treatment beam source. Other types of medical devices are conceivable. The system may further comprise a subject support unit 7. The system may comprise a display device 8 connected to or integrally formed with the computing system. Figure d, for the sake of illustration, shows that a user interface 9 may be displayed by the display device and that the user interface may include a user input element 10. Alternatively or in addition, the system may comprise other user input elements, for example a keyboard, a mouse, a touchpad and/or one or more physical buttons.

The components of the medical system 1 may be configured as described above and, in particular, may be configured to carry out the method of the present disclosure.

In particular, the computing system 2 may be configured to carry out and/or control the steps of the method of the present disclosure. The imaging devices, in particular the CT imaging device 5, may be configured to acquire image data to be used for the planning image data. The imaging devices, particularly the X-ray imaging device 3 and the surface camera 4, may be configured to acquire the initial image data and to acquire image data for monitoring the subject position, i.e., for obtaining monitoring image data. They may also be used for aiding a pre-positioning of the subject (prior to correction).

Exemplary method steps of yet another method of the present disclosure are described below. FIGS. 4a to 4h show exemplary user interfaces associated with some of these steps. The user interfaces, according to the present disclosure, may be displayed on a display device of the medical image system.

Figure 4A:
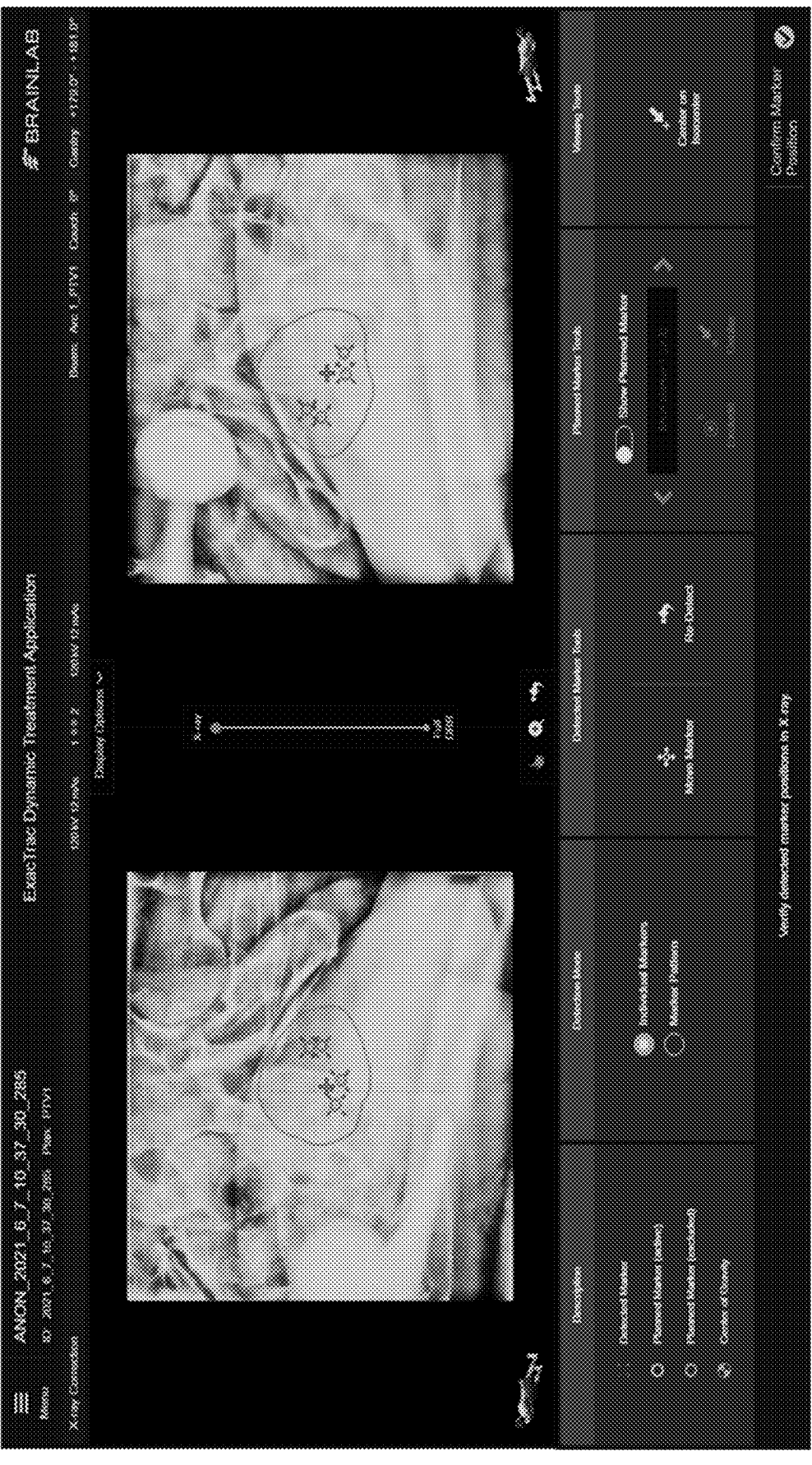
FIGS. 4a to 4h show examples of user interfaces.
Figure 4B:
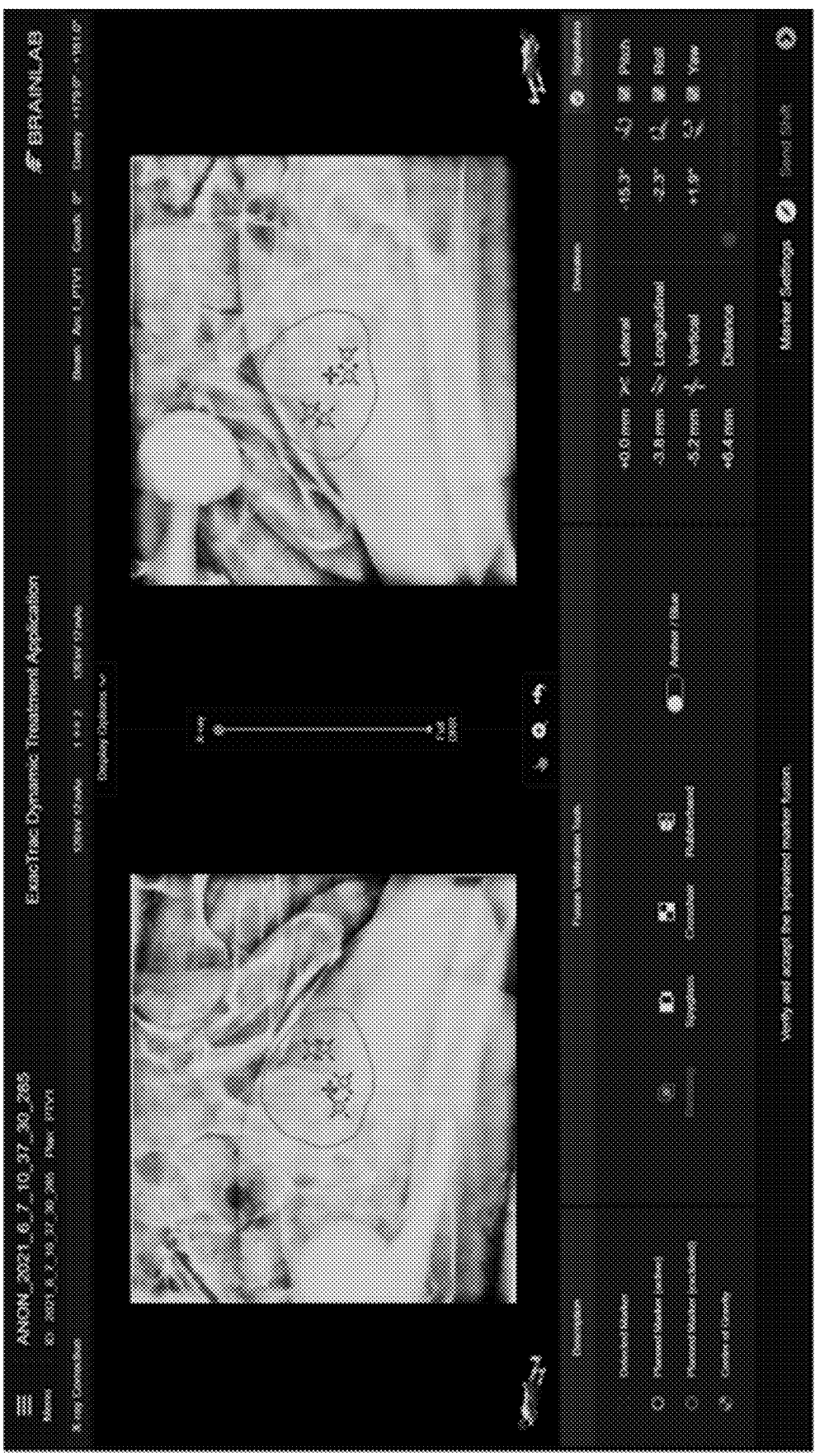
Figures 1, 4C:
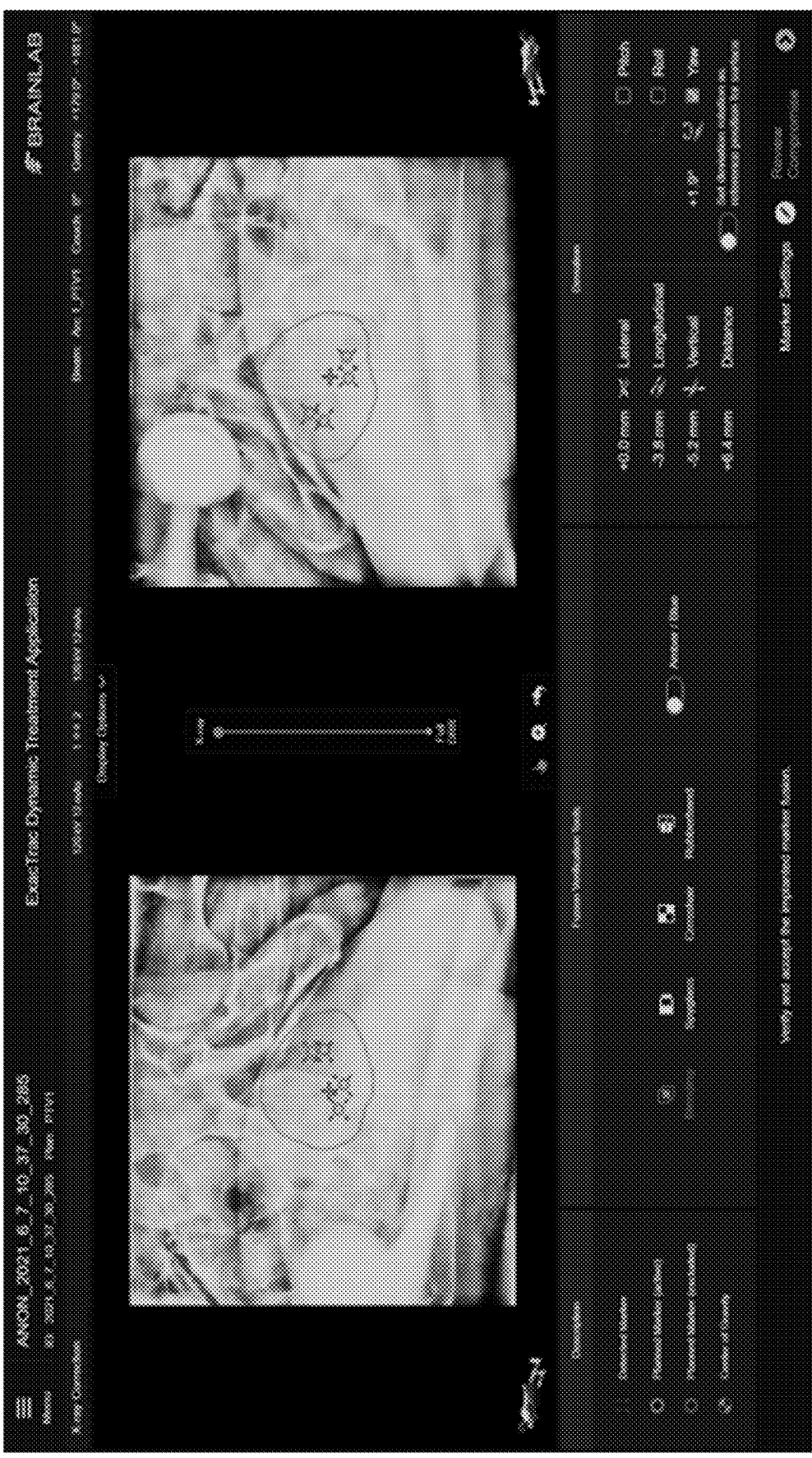
Figure 4D:
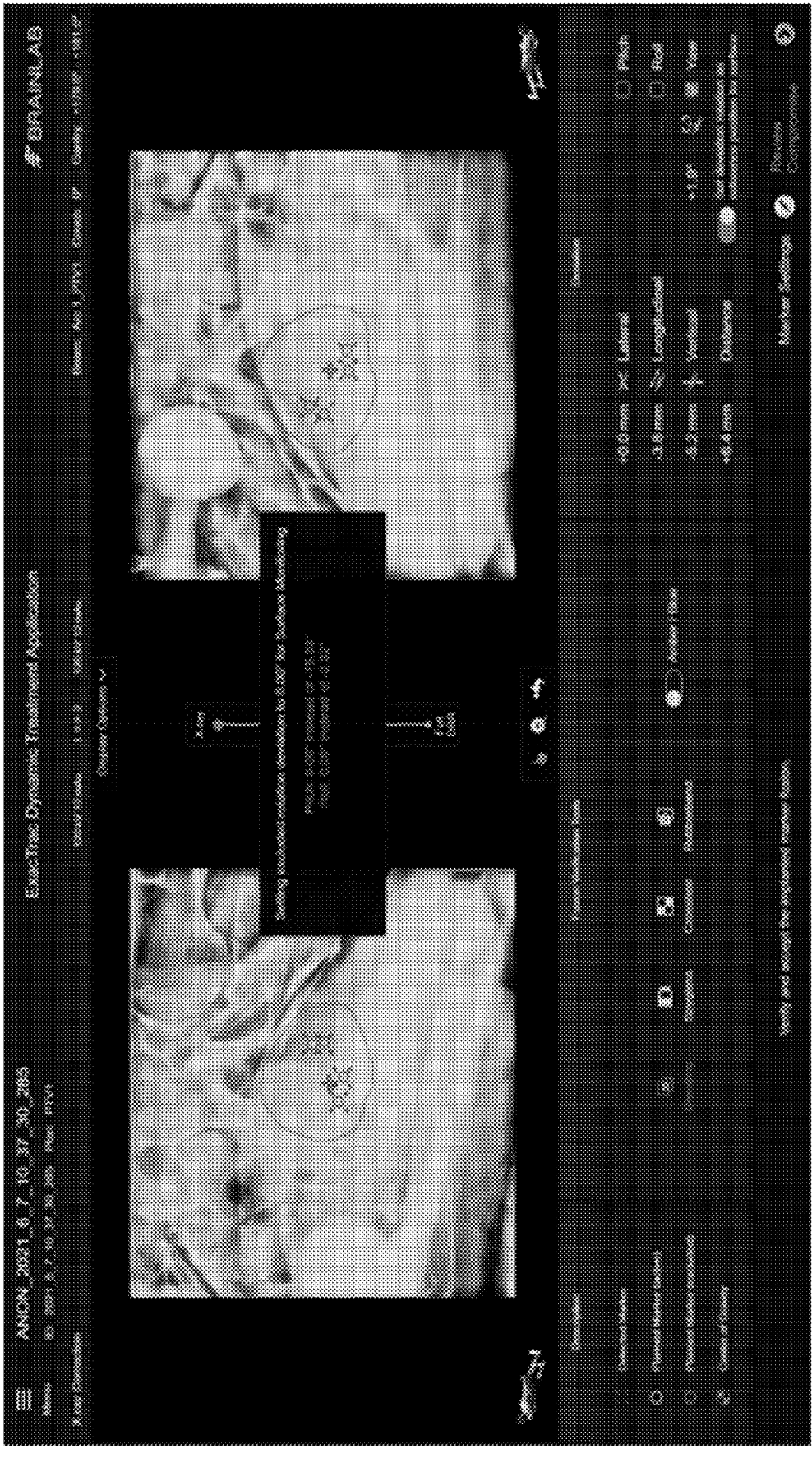
Figure 4E:
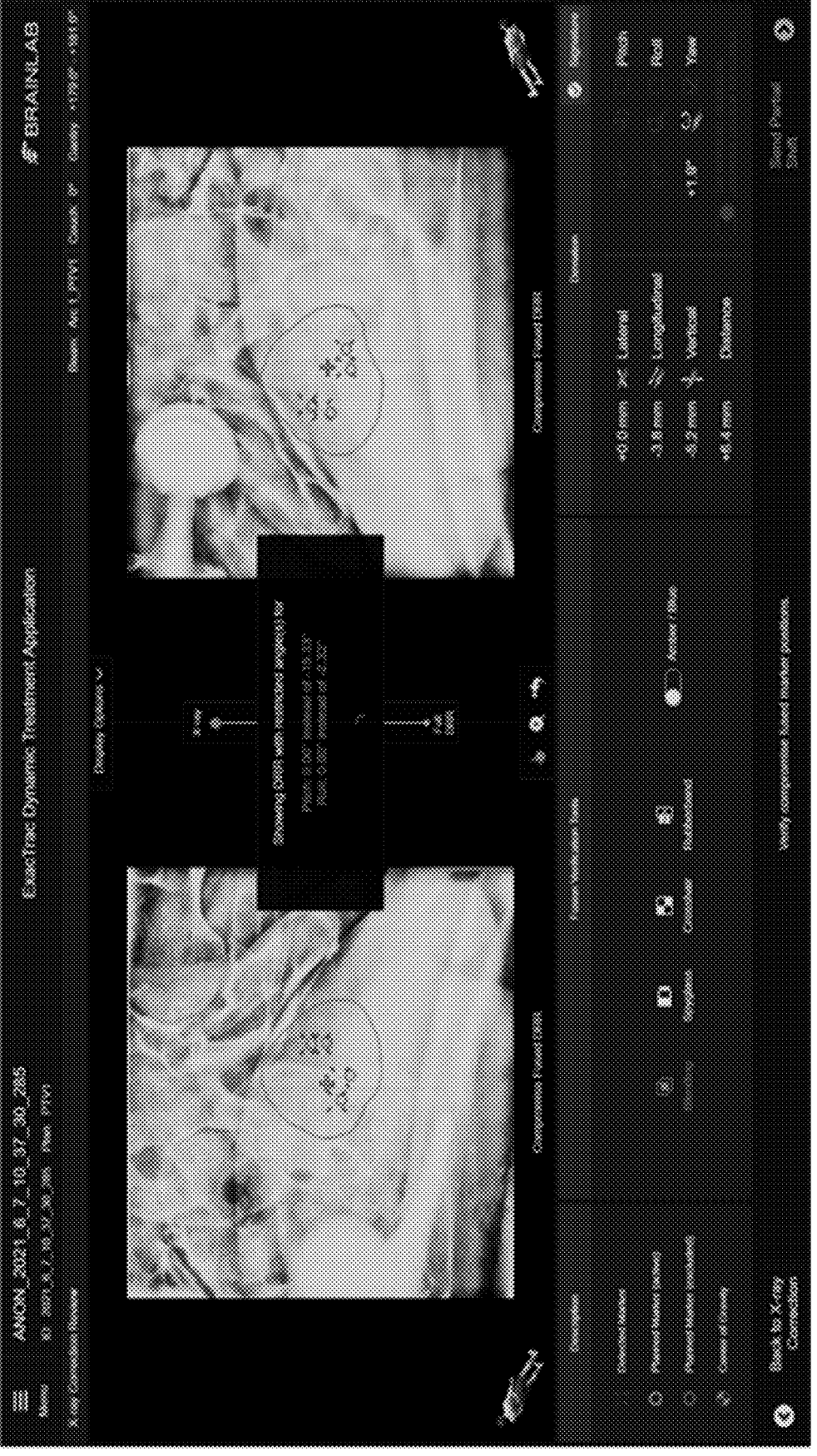
Figure 4F:
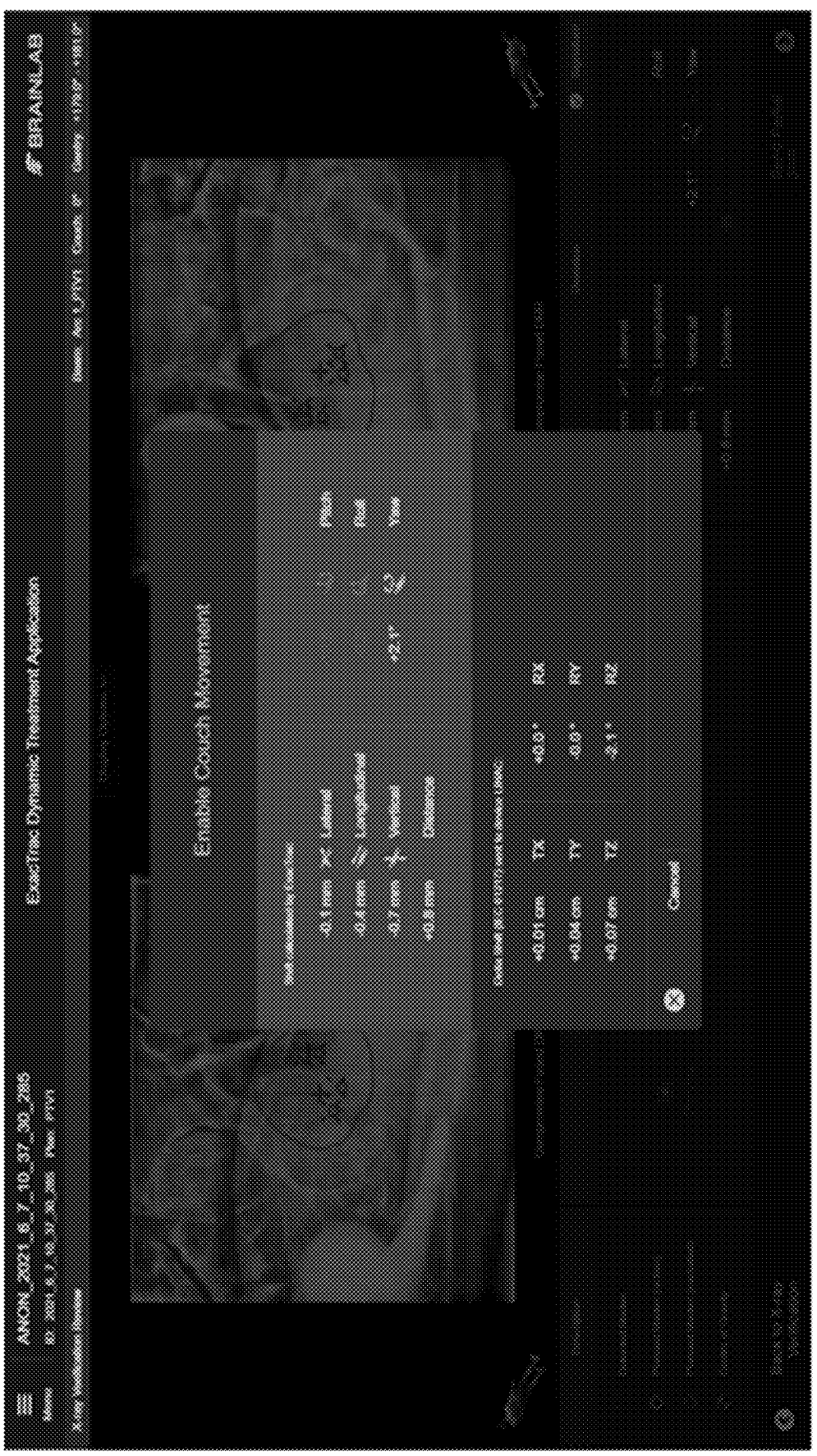
Figure 4G:
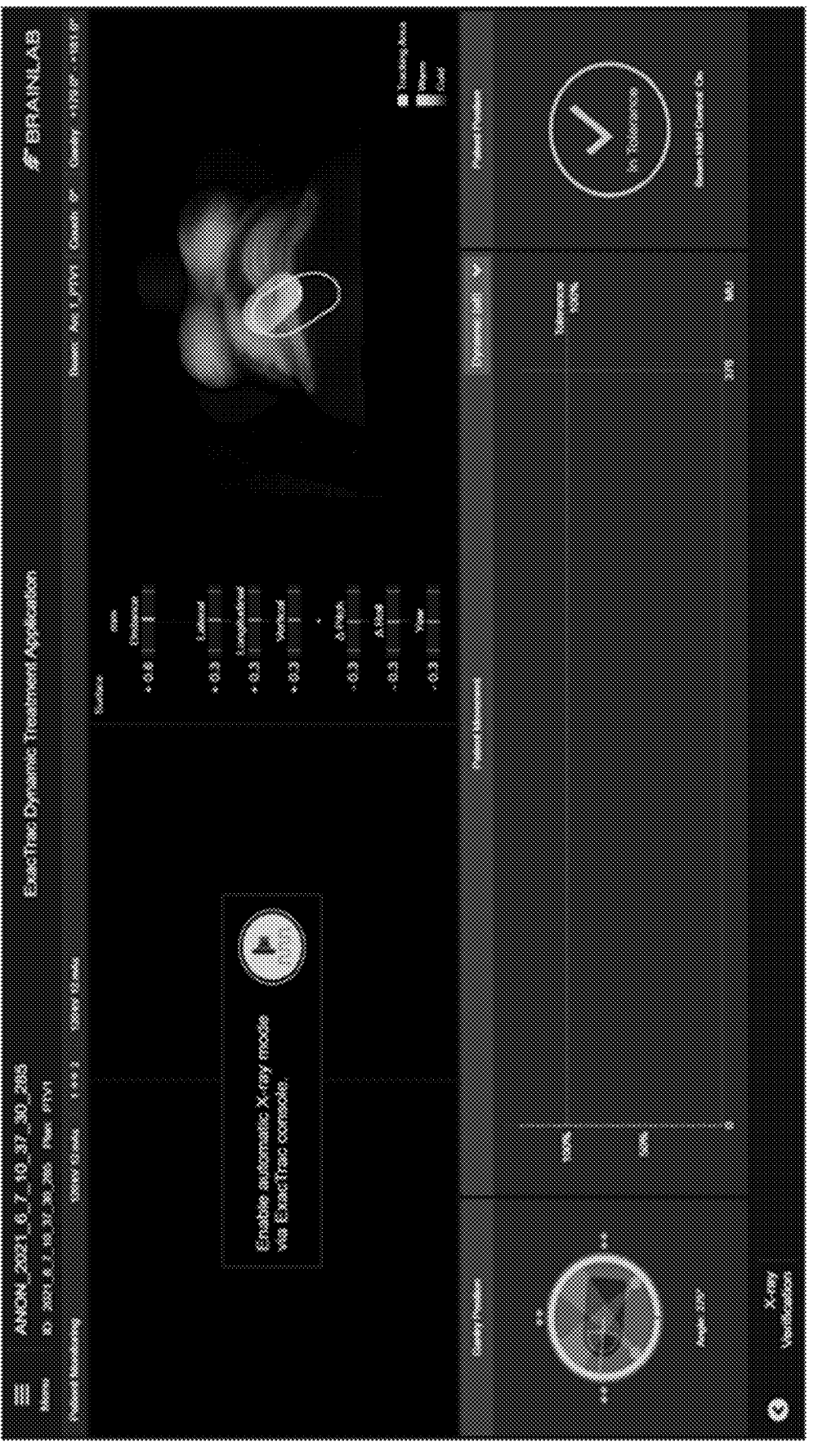
Figure 4H:
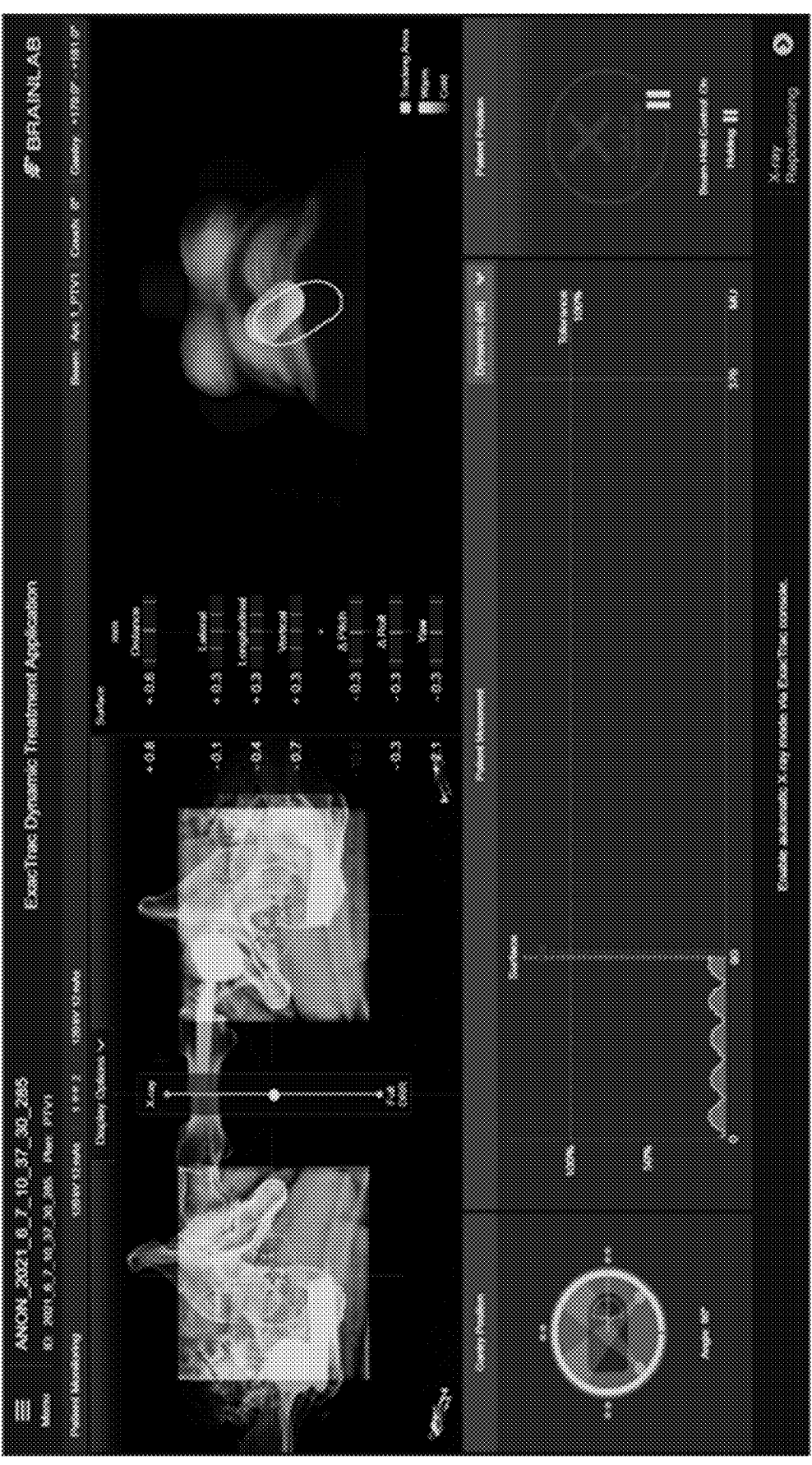

To briefly summarize the user interfaces, FIG. 4a shows the initial user interface, for example at a time after pre-positioning the subject and prior to a position correction procedure. FIG. 4b shows that pitch, roll, and yaw, i.e., the three possible rotations, are all selected, as indicated by the checked boxes. The selection is performed via a user input. Thus, the user selects or defines the correction data, specifically, the corrections to be included and excluded from the correction procedure. Selected rotations will be corrected, deselected rotations will be excluded from the correction procedure. In the user interface shown in FIG. 4c-1, and a detailed view of a portion thereof as shown in FIG. 4c-2, pitch and roll are deselected, so as to be excluded from the correction procedure, and a toggle button, which indicates whether the selection, and accordingly the partial correction, is to be applied to the monitoring, is set so as to apply the partial correction. The deselection and operation of the toggle button are performed via user input. In FIG. 4d, the excluded rotations are set to 0.0° for the surface monitoring. FIG. 4e shows the images after correction. As seen on the right-hand side, a signature may be required (applied via a user input) to confirm the partial correction. FIG. 4f summarizes the corrections. FIG. 4g shows the user interface at the beginning of the monitoring and FIG. 4h shows the user interface during the monitoring. These user interfaces are merely non-limiting examples.

In more detail, according to the method of this example, the subject is a patient and the predetermined portion of the subject is a prostate, but other extracranial inner organs may likewise be the predetermined portion. It is noted that the imaging, planning, and positioning explained under items 1 to 3 below may be performed in accordance with known methods.

1. Pre-Positioning and Initial Image Acquisition a) Patient, e.g. with implanted markers, is positioned on the RT treatment table. The predetermined portion may be the prostate and the markers may be implanted in the prostate. Alternatively, the predetermined portion may be, e.g., the pancreas, gallblader, lung, or liver. The implanted markers are radiopaque. The predetermined portion may be or comprised in a region of interest (ROI) selected in planning data or may comprise markers.

b) Pre-positioning, for example based on laser markers (tattoos) or surface camera, is performed and confirmed by a user. The computing system calculates a deviation from planning data.

As an example, a surface camera may be employed. A reference contour determined from a planning CT may be compared to a live measured surface contour obtained by the surface camera. The comparison may comprise a calculation and/or showing representative images on a display. Alternatively, it may be based on predetermined reference, e.g. projections, for example as provided by an augmented reality device overlaying a virtual image onto a field of view of a user or camera.

c) Optionally, an Area of Interest (AOI) is selected on the surface, e.g., by the user. The AOI may be any surface area particularly suitable for surface monitoring, e.g., due to its shape and/or location.

d) Image of the internal patient anatomy including the region of interest (ROI), e.g., including the internal organ, is acquired by volume imaging, e.g. Stereoscopic X-ray images, e.g. monoscopic X-ray, portal imaging, ultrasound, MRI, or CBCT. Concurrently, a corresponding surface image of the AOI may be acquired and stored. The AOI is not necessarily linked to the region of interest, but it can be linked. That is, the AOI and ROI may be selected independently. For example, the ROI may be in a different area of the subject, for example in a different body part, than the AOI.

2. Detecting Position Deviation (Option 1): ROI Identification a) Planning data comprises a planning CT and a matching step (e.g. finding DRR that matches acquired 2D X-ray, or CBCT) to determine 6 DOF position of internal structure. In the planning data, the ROI may be defined for the soft tissue that may move independently from the body surface. As an example, 2D-3D matching may be performed, e.g. finding DRR projection parameters that produce a DRR that matches the acquired X-ray in the region of interest.

b) Detecting the position deviation may then comprise detecting a mismatch based on the (e.g., DRR) matching.

3. Detecting Position Deviation (Option 2): Marker Match a) Planning image data comprises CT image data obtained when markers were inside the patient, particular located at the predetermined portion.

b) In a detection mode, markers may be determined individually via image analysis. For example, all markers are detected in the 2D or 3D images (see 1d), and the position in 3D is determined, optionally using registration to the planning CT.

Optionally the images may be prefiltered for appropriate marker candidates considering location and shape factors e.g. arc length, roundness or convexity defects.

The marker search may be initialized with the allocation of the images into marker search areas, originating from planned marker 3D positions or (if available) last calculated transformation matrix. The detected marker candidates are reprojected to 3D space to localize 3D marker candidates at intersection points. Obtained marker candidates are compared with both, the planned positions of the single markers as well as the configuration consisting of all planned markers. Those 3D marker candidates, that match a position in relation to the planned marker configuration, are kept and registered.

c) Computing system calculates match of detected markers to markers in planning image (e.g., CT image data). A mismatch indicates a deviation of a position of a predetermined portion of a subject from a predetermined position of the predetermined portion of the subject. The mismatch or deviation has 6 DOF, i.e., 3 translations and 3 rotations.

d) For example, the system may calculate the transformation matrix between the detected and registered markers and the markers in the planning image (e.g., CT image). The match is 6D, i.e. three translations and three rotations.

4. Preparation for Monitoring

Large rotational deviations (yaw, roll, and/or pitch) are detected, e.g. above a (potentially application-specific) threshold of 5° or 3°. Large rotations are clinically not so relevant for round targets like the prostate. For example, the user can select to not correct these rotations. It is noted that in many cases the transformation may be defined in such a way that rotations are rotations around the isocenter, i.e., the rotation axis extends through the isocenter. The isocenter is the rotation center of the couch on which the subject is positioned. The region of interest, e.g., the organ, particularly a tumor located therein, will generally also be arranged in the isocenter.

As an example:

a) One or more rotations may be indicated as being excluded from a correction procedure, e.g. via user selection.

b) The user selects the function "Set excluded rotations as surface reference".

c) Deviations of excluded rotations are set to '0.0°'

Excluded rotations will not be corrected during the correction procedure, which may, for example, be performed by moving a couch on which the subject is positioned. That is, the couch may receive a control signal that only contains the translations and the rotations that are not excluded.

d) A partial transformation representing the partial correction (i.e., without the excluded rotation) is performed on the X-ray image (from step 1d) or a 2D projection/reconstruction of planning data (e.g., DRR from CT). The transformed X-ray image or projection/reconstruction image data is overlayed with the non-transformed projection/reconstruction image data or X-ray image. The result may be displayed to the user as an image overlay. Optionally, in addition, a full transformation may also be performed (including the excluded rotation) on the same image data and the image data may be registered and displayed as an overlay in an alternative view. The user can then compare views.

e) The user may confirm the exclusion and the correction data (excluding the excluded rotation) may be sent to a couch controller for performing the position correction.

f) Upon user confirmation, the stored surface image of step 1d may be initialized based on the applied partial correction, in other words, the partial correction (excluding the excluded rotation) may be applied to the surface image. The result may be used as a reference for monitoring. It is noted that alternatively the stored surface image may be used as a reference for monitoring, i.e., without applying the correction to the initial surface image data, and the correction data may be used alongside the stored surface image for use in monitoring.

5. Optional Preparation for and Monitoring Using X-Ray Data

In addition to applying the partial correction to the surface image data of step 1d, the partial correction may also be applied to the X-ray image data of step 1d. That is, an X-ray reference position may be updated based only on the applied partial correction as well. In other words, for the current session, the accepted position is updated. For example. the first X-ray for patient setup (step 1d) is misaligned, e.g. by the excluded rotation. During monitoring, further X-ray images may be acquired for monitoring the patient position. The excluded rotation of the initial misalignment is ignored during this monitoring. For example, the reference CT (obtained in the planning stage) is rotated, or the X-ray (obtained prior to monitoring or obtained during monitoring) is rotated or the correction data is taken into account during the monitoring rather than rotating the images.

6. Monitoring a) As an example, monitoring with isometric match in 6 DOF may be performed. For example, this may comprise continuous measurement of a patient surface with the surface camera (e.g. at 20 Hz and optionally using an additional thermo-camera) and optionally X-ray images may be obtained (e.g., at fixed times or time intervals or triggered manually).

b) In the surface monitoring user interface, changes in patient position may be output, including rotations. For the previously excluded rotations, only the (relative) deviation from the accepted position may be shown and indicated to the user, for example via a "delta". For example, if no patient movement is detected, the display may show "Δ 0.0°".

c) Optionally, color coding of a surface deviation may be shown on the user interface, for example in the form of a color map. The color coding may be configured to exclude the ignored/excluded rotations.

d) Optionally a global similarity may be calculated between the reference data and the measured surface (e.g., RMS).

e) Optionally X-ray monitoring may also be performed (see 5).

f) Optionally any successful registration of a stereo-scopic X-Ray fusion may update the reference of the surface tracking system and reset the excluded rotations to 0.0°. In this context, a successful registration means that the image is within tolerance.

g) Optionally, a switch button may displayed on the user interface for switching views, for example for switching between views showing the real or the corrected deviation.

7. Patient Movement During Monitoring

Any patient movement detected in the surface or X-ray monitoring may trigger, in response to determining that it is out of tolerance, outputting a warning and/or creating signals for controlling medical equipment, e.g., the beam source.

The above-mentioned methods may be carried out by a system according to the present disclosure or any other suitable system and the system described above may be configured to carry out any of the methods above or any other method according to the invention.

While the invention has been illustrated and described in detail in the drawings and foregoing description, such illustration and description are to be considered exemplary and not restrictive. The invention is not limited to the disclosed embodiments. In view of the foregoing description and drawings it will be evident to a person skilled in the art that various modifications may be made within the scope of the invention, as defined by the claims.

The invention claimed is:

1. A computer-implemented method for monitoring a subject position, the method comprising:

determining a deviation of a position of a predetermined portion of a subject from a predetermined position of the predetermined portion of the subject;

based on the deviation, determining correction data, the correction data specifying one or more corrections to be performed on the subject position as part of a position correction procedure and specifying one or more rotational corrections as being excluded from the position correction procedure; and setting reference data as a reference for subsequent monitoring of changes of the subject position, wherein the reference data comprises the correction data and initial image data acquired prior to performing the position correction procedure and/or corrected initial image data that has been corrected based on the correction data; and rendering, on a user interface, a view related to the position correction procedure based on the correction data or subsequent monitoring of changes of the subject position based on the reference data, wherein the position correction procedure includes sending control signals to a subject support unit that operates drives to change the position of the subject based on the control Signals.

2. The method of claim 1, wherein determining correction data comprises determining, for each rotational deviation of the predetermined portion of the subject, whether the rotational deviation should be corrected by means of the position correction procedure and, in response to determining that the rotational deviation should not be corrected, specifying a corresponding rotational correction as being excluded from the position correction procedure.

3. The method of claim 2, wherein determining whether the rotational deviation should be corrected comprises receiving a user selection via the user interface and/or is performed automatically on the basis of pre-determined criteria by determining whether the rotational deviation
exceeds a predetermined threshold.

4. The method of claim 1, wherein determining the
deviation comprises:
    determining the position of the predetermined portion of
        the subject based on the initial image data of the
        predetermined portion of the subject, and
    determining the position of the predetermined portion of
        the subject based on planning image data of the pre-
        determined portion of the subject acquired prior to
        acquiring the initial image data.

5. The method of claim 4, wherein each of the planning
image data and the initial image data comprise image data of
an inner organ of the subject and the predetermined portion
includes the inner organ of the subject, and wherein the
deviation is determined at least based upon a position of the
inner organ.

6. The method of claim 5, wherein the planning image
data further comprises surface image data of the subject.

7. The method of claim 1 comprising, after determining
the deviation, triggering an automatic position correction
procedure of the subject position, based on the correction
data, wherein the position correction procedure excludes the
one or more rotational corrections specified as being
excluded from the correction procedure in the correction
data.

8. The method of claim 1, wherein the monitoring of
changes of the subject position is based on monitoring image
data,
    wherein the reference data and the monitoring image data
        each comprise surface image data of the subject, and
    wherein monitoring the subject position comprises sur-
        face imaging, including detecting deviations of the
        surface image data of the monitoring image data from
        the surface image data of the reference data.

9. The method of claim 8, wherein the monitoring of
changes of the subject position is further based on monitor-
ing image data,
    wherein the reference data and the monitoring image data
        each comprise volume image data of the subject,
    wherein monitoring the subject position comprises vol-
        ume imaging, including detecting deviations of the
        volume image data of the monitoring image data from
        the volume image data of the reference data,
    wherein the monitoring comprises the surface imaging
        and the volume imaging, and
    wherein the surface imaging is configured to obtain image
        data more frequently than the volume imaging.

10. The method of claim 1, wherein the monitoring of
changes of the subject position is based on monitoring image
data,
    wherein the reference data and the monitoring image data
        each comprise volume image data of the subject, and
    wherein monitoring the subject position comprises vol-
        ume imaging, including detecting deviations of the
        volume image data of the monitoring image data from
        the volume image data of the reference data.

11. The method of claim 1, wherein the monitoring of
subject position comprises, in response to the subject posi-
tion moving out of a predetermined tolerance, triggering an
output of a warning and/or output of a correction suggestion
to an operator and/or triggering an automatic position cor-
rection procedure, the automatic position correction proce-
dure comprising rotations.

12. The method of claim 11, wherein one or more rota-
tional and/or translational changes of the subject position,
determined by a user selection or automatically based on predetermined criteria, are excluded from triggering an
output of a warning and/or output of a correction suggestion
to an operator and/or triggering an automatic position cor-
rection procedure.

13. The method of claim 1, wherein the reference data
comprises volume image data that is used as a reference for
volume imaging-based monitoring, and wherein surface
image data corresponding to the volume image data of the
reference data is set as a reference for monitoring by means
of surface imaging or a deviation in the surface image data
corresponding to the volume image data is set as acceptable
or a deviation in the surface image data corresponding to the
volume image data is set to zero or a deviation in the surface
image data corresponding to the volume image data is set to
the deviation of the volume image data, or
    wherein the reference data comprises surface image data
        that is used as a reference for surface-based monitoring,
        and wherein volume image data corresponding to the
        surface image data of the reference data is set as a
        reference for monitoring by means of volume imaging
        or a deviation in the volume image data corresponding
        to the surface image data is set as acceptable or a
        deviation in the volume image data corresponding to
        the surface image data is set to zero or a deviation in the
        volume image data corresponding to the surface image
        data is set to the deviation of the surface image data.

14. The method of claim 1, comprising:
    rendering, on the user interface, a first view, wherein
        planning image data are overlayed with monitoring
        image data, and/or a second view, wherein initial image
        data are overlayed with monitoring image data, and/or
        a third view, wherein corrected initial image data are
        overlayed with planning image data and/or a fourth
        view, wherein corrected initial image data are over-
        layed with monitoring image data, and/or a fifth view,
        wherein initial image data are overlayed with monitor-
        ing image data corrected using the correction data,
        and/or
    rendering a view in which the monitoring image data
        overlayed with the planning image are corrected by the
        excluded rotation and/or a view in which the corrected
        initial image data to be overlayed with the planning
        image data are corrected by the excluded rotation,
        and/or
    rendering, on the user interface, a user interface element
        indicating that one or more rotational corrections are
        currently excluded from the position correction proce-
        dure and/or indicating information on the one or more
        rotational corrections that are currently excluded,
        including the corresponding rotation axis and/or the
        direction and/or the amount of the deviation.

15. The method of claim 14, comprising rendering, on the
user interface, a selection option for switching between at
least two of the first view, the second view, the third view,
the fourth view, and the fifth view, and/or
    comprising rendering, on the user interface, a user inter-
        face element indicating which of the views is currently
        rendered.

16. The method of claim 1, comprising:
    acquiring planning image data, including volume image
        data and surface image data; and/or
    acquiring the initial image data, including volume image
        data and surface image data after acquiring the plan-
        ning image data; and/or
    in response to a triggering of an automatic position
        correction procedure, performing the position correc-
        tion procedure by automatically moving the subject support unit so as to correct the subject position, the position correction procedure excluding the one or more rotational corrections specified as being excluded from the correction procedure in the correction data; and/or acquiring monitoring image data, including volume image data and surface image data, after acquiring the planning image data, the monitoring image data being acquired continuously and/or at least at predetermined times and/or intervals; and/or creating control data for controlling medical equipment.

17. A medical system comprising:

a computing system comprising a processor and a memory device, wherein the processor is operable to execute program logic stored in the memory device to perform the steps comprising:

determining a deviation of a position of a predetermined portion of a subject from a predetermined position of the predetermined portion of the subject;

based on the deviation, determining correction data, the correction data specifying one or more corrections to be performed on the subject position as part of a position correction procedure and specifying one or more rotational corrections as being excluded from the position correction procedure; and setting reference data as a reference for subsequent monitoring of changes of the subject position, wherein the reference data comprises the correction data and initial image data acquired prior to performing the position correction procedure and/or corrected initial image data that has been corrected based on the correction data; and render, on a user interface, a view related to the position correction procedure based on the correction data or subsequent monitoring of changes of the subject position based on the reference data, wherein the position correction procedure includes sending control signals to a subject support unit that operates drives to change the position of the subject based on the control signals; and one or more imaging devices configured to be triggered and/or controlled by means of the computing system to obtain the initial image data and/or monitoring image data.

18. The medical system of claim 17 further comprising:

a medical device for radiation treatment of a subject controlled by means of the computing system; and/or the subject support unit configured to automatically correct a subject position triggered and/or controlled by means of the computing system.

19. A non-transitory computer-readable storage medium having stored thereon program logic stored in a memory device of a computer that when executed by a computer or when loaded onto the computer, causes the computer to carry out a method for monitoring a subject position, the method comprising:

determining a deviation of a position of a predetermined portion of a subject from a predetermined position of the predetermined portion of the subject;

based on the deviation, determining correction data, the correction data specifying one or more corrections to be performed on the subject position as part of a position correction procedure and specifying one or more rotational corrections as being excluded from the position correction procedure; and setting reference data as a reference for subsequent monitoring of changes of the subject position, wherein the reference data comprises the correction data and initial image data acquired prior to performing the position correction procedure and/or corrected initial image data that has been corrected based on the correction datal and rendering, on a user interface, a view related to the position correction procedure based on the correction data or subsequent monitoring of changes of the subject position based on the reference data, wherein the position correction procedure includes sending control signals to a subject support unit that operates drives to change the position of the subject based on the control signals.

\* \* \* \* \*